(12) United States Patent
Anderson et al.

(10) Patent No.: US 8,613,520 B2
(45) Date of Patent: Dec. 24, 2013

(54) PROCESS OF FORMING A LIGHT BEAM PATH IN A DIELECTRIC MIRROR

(75) Inventors: Tyler Anderson, Lincoln, NE (US); Ahmed Bouzid, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 993 days.

(21) Appl. No.: 12/172,103

(22) Filed: Jul. 11, 2008

(65) Prior Publication Data

US 2010/0007958 A1    Jan. 14, 2010

(51) Int. Cl.
*G02B 5/08*    (2006.01)

(52) U.S. Cl.
USPC ............... 359/839; 359/581; 372/93

(58) Field of Classification Search
USPC ............ 359/580–581, 584, 884, 731, 729; 372/93, 98, 99, 103
See application file for complete search history.

(56) References Cited

U.S. PATENT DOCUMENTS

| | | | |
|---|---|---|---|
| 2,801,570 A * | 8/1957 | Nomarski et al. | 359/731 |
| 2,968,220 A * | 1/1961 | Steglich | 359/730 |
| 4,588,267 A | 5/1986 | Pastore | |
| 4,934,816 A | 6/1990 | Silver et al. | |
| 5,073,012 A | 12/1991 | Lynam | |
| 5,835,230 A | 11/1998 | McAndrew et al. | |
| 6,064,488 A | 5/2000 | Brand et al. | |
| 7,379,224 B2 | 5/2008 | Tonar et al. | |
| 2003/0043315 A1 | 3/2003 | Umemoto et al. | |
| 2004/0001265 A1 | 1/2004 | Pesik | |
| 2005/0078389 A1 | 4/2005 | Kulas et al. | |
| 2007/0029289 A1 * | 2/2007 | Brown | 219/121.6 |
| 2007/0091404 A1 * | 4/2007 | Miyamoto | 359/204 |
| 2007/0242720 A1 | 10/2007 | Eckles et al. | |
| 2008/0080077 A1 | 4/2008 | Shih et al. | |

FOREIGN PATENT DOCUMENTS

| | | |
|---|---|---|
| JP | 56-013505 A | 2/1981 |
| JP | 08-043293 A | 2/1996 |
| JP | 09-251105 A | 9/1997 |
| JP | 2004-053405 A | 2/2004 |
| JP | 2004-070322 A | 3/2004 |
| JP | 2007-242720 A | 9/2007 |
| WO | WO 00/31569 A1 | 6/2000 |

OTHER PUBLICATIONS

Fraunhofer IPM, "Components Multi reflection cells," Dec. 2007, located at <http://www.ipm.fraunhofer.de/fhg/ipm_en/solutions_services/processmonitoring/opt_compo...>, last accessed on Feb. 1, 2008, 1 page.

(Continued)

*Primary Examiner* — Jennifer L. Doak
(74) *Attorney, Agent, or Firm* — Leydig, Voit & Mayer, LLP; Gerald T. Gray (57) ABSTRACT

An optical mirror element includes an optically transmissive element having a first surface and a second surface, and a reflective coating layer on the first surface that defines a mirror surface. A first portion of the first surface does not include the reflective coating layer such that the first portion defines an optically transmissive window in the mirror surface. Q method of forming an optical mirror element having a window portion includes providing an optical element, masking a first portion of a first surface of the optical element, and thereafter applying a reflective coating to the first surface so as to define a reflective surface, wherein the masked portion defines a transmissive region in the reflective surface. The exposed portion of the first surface may be coated with an anti-reflective coating, either before or after the reflective coating is applied.

6 Claims, 7 Drawing Sheets

(56) References Cited

OTHER PUBLICATIONS

Agarwal, Rahul et al., "Fabrication of Integrated Vertical Mirror Surfaces and Transparent Window for Packaging MEMS Devices," *Journal of Microelectromechanical Systems*, Feb. 1, 2007, 16(1):122-129.

European Search Report and Written Opinion for EP Application No. 08160699, dated May 31, 2012, 5 pages.

Hecht, Eugene, "Ch. 9.7 Applications of Single and Multilayer Films," *Optics*, Jan. 1, 1998, p. 418.

"Sphärische Hohlspiegel-Substrate," Product Information Sheet, Dec. 31, 2006, p. 1. Retrieved from the Internet: URL:http://www.b-halle.de/EN/Downloads/Spherical_Concave_Mirror_Substrates.pdf.

Extended European Search Report and Written Opinion for EP Application No. 08160699.8, dated Oct. 2, 2012, 12 pages.

Morris et al., "Engineered diffusers for display and illumination systems: Design, fabrication and applications," wwwrpcphotonics.com, pp. 1-11, (2011).

\* cited by examiner

PROCESS OF FORMING A LIGHT BEAM PATH IN A DIELECTRIC MIRROR

This work was supported in part by a grant from the SKR/DOE, DE-FG02-05ER84283. The government may have certain rights in this invention.

BACKGROUND OF THE INVENTION

The present invention relates generally to optical devices, and more particularly to optical mirror elements having optically transmissive windows or features.

Devices such as gas analyzers typically include internal cavities defined by two end mirrors. A laser beam or other light source enters the cavity and reflects back and forth between the mirror end faces to provide a long path length. A long path length allows for better absorption of the light by trace gases, and hence detection of trace gases. Path lengths of between about 1 meter and 100 meters are typical and path lengths on the order of a kilometer are possible. For a confocal cavity arrangement, such as may be found in a Herriott Cell, beam entry into the cavity is typically off axis at a certain entry point. The beam reflects off of the concave-shaped end mirrors at discrete reflection points until it exits the entry point or other defined aperture. Typically, the entry point, and other aperture(s), are formed by drilling a hole in the mirror element to allow for entry of light into the cavity.

For in-the-field applications, such as use of a portable gas analyzer to test trace gases on site, it is desirable to maintain a controlled environment within the Herriott Cell cavity. To realize such applications, the physical hole(s) are filled with a glass plug to keep the cavity environment contained and to make the device robust for field use (i.e., to prevent contaminants from entering the cavity). However, use of a glass plug can be difficult and costly, and it may introduce noise due to reflections around the perimeter of the hole. Additionally, the process of drilling and filling with a glass plug can be costly and time-consuming, and may limit the cavity sizes that can be used.

Therefore it is desirable to provide methods and devices that overcome the above and other problems. In particular, it is desirable to provide mirror elements, and methods of manufacturing the same, that are simple and cost-effective.

BRIEF SUMMARY

The present invention provides optical mirror elements having a transmissive window, methods for making optical mirror elements, and devices incorporating such optical mirror elements. The optical mirror elements are particularly well suited for use in Herriott Cell arrangements.

According to one embodiment, an optical mirror element is provided that typically includes an optically transmissive element having a first surface and a second surface, and a reflective coating layer on the first surface that defines a mirror surface, wherein a first portion of the first surface does not include the reflective coating layer such that the first portion defines an optically transmissive window in the mirror surface.

According to another embodiment, an optical cavity device is provided. The device typically includes a first mirror element having an internal surface and an exterior surface, wherein a first portion of the interior surface comprises a reflective coating defining a reflective surface, and wherein a second portion of the internal surface comprises an anti-reflective coating defining an optically transmissive window in the reflective surface, and a second mirror element having an internal surface and an exterior surface. The device also typically includes a housing structure configured to hold the first and second mirrors such that the internal surfaces are facing each other along a common axis. One example of such a device structure is a Herriott Cell arrangement.

According to yet another embodiment, a method of forming an optical mirror element having a window portion is provided. The method typically includes providing an optical element, masking a first portion of a first surface of the optical element, and thereafter applying a reflective coating to the first surface so as to define a reflective surface, wherein the masked portion defines a transmissive region in the reflective surface. In certain aspects, the exposed portion of the first surface is coated with an anti-reflective coating, either before or after the reflective coating is applied.

According to yet another embodiment, a method of forming an optical mirror element having a window portion is provided. The method typically includes providing an optical element, applying a reflective coating to a first surface of the optical element so as to define a reflective surface, and removing a first portion of the reflective coating so as to expose a portion of the first surface of the optical element, wherein the exposed portion of the first surface defines a transmissive region in the reflective surface. In certain aspects, the exposed portion of the first surface is coated with an anti-reflective coating, either before or after the reflective coating is applied.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

The present invention provides optical mirror elements having a transmissive window, methods for making optical mirror elements, and devices incorporating such optical mirror elements. The optical mirror elements are particularly well suited for use in Harriet cell arrangements.

Figure 1A:
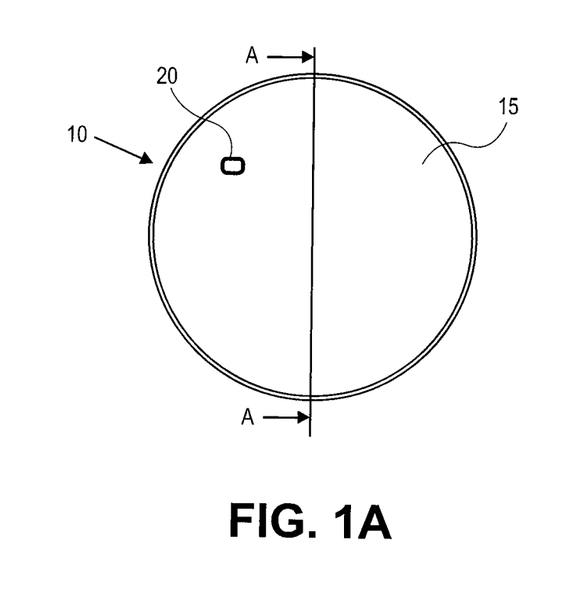
FIGS. 1A and 1B illustrate an optical mirror element having a window portion according to one embodiment.
Figure 1B:
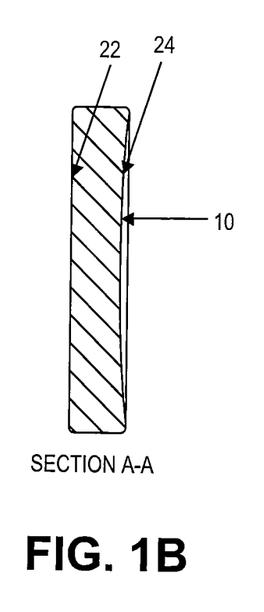

FIG. 1 illustrates an optical mirror element having a window portion according to one embodiment. As shown mirror element 10 has a reflective mirror surface 15 with a window or aperture 20 that allows light to pass through the mirror surface. Window 20 may take on a circular, rectangular or any other shape as is desired. FIG. 1a shows a frontal view of the mirror surface and FIG. 1b shows a side view of the mirror element. In one embodiment, the reflective mirror surface 15 includes a reflective coating layer that defines a mirror surface. A first portion of the mirror surface does not include the reflective coating layer such that that portion defines an optically transmissive window 20 in the mirror surface. The mirror element 10 shown in FIG. 1 has a flat end face 22 and a concave face 24 on which the mirror surface 15 is defined. One skilled in the art will recognize that the mirror element may have any other shape as desired.

Figure 2:
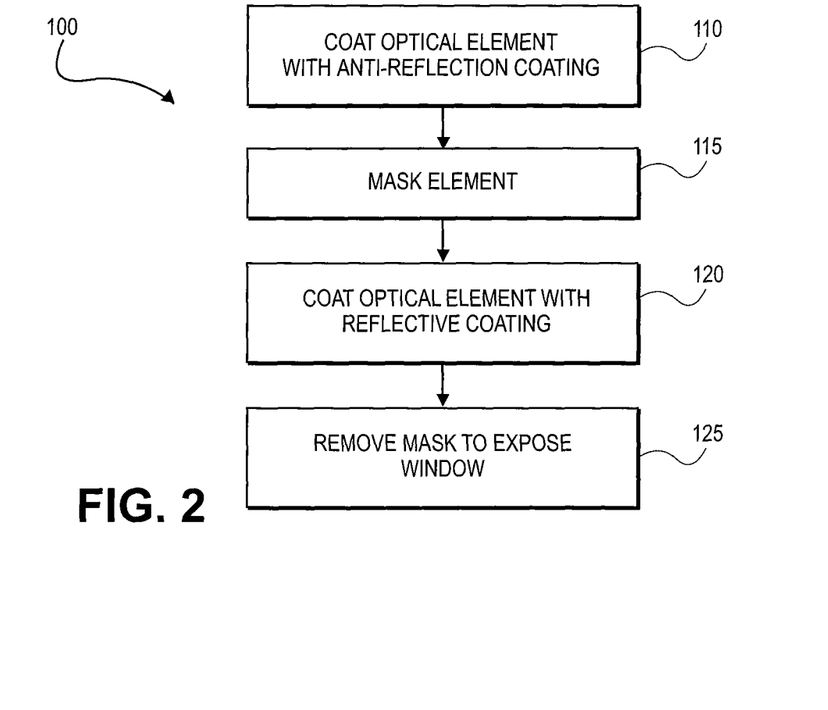
FIG. 2 illustrates a method of fabricating a mirror element having a window according to one embodiment.

FIG. 2. illustrates a method 100 of fabricating a mirror element 10 having a window 20 according to one embodiment. In step 110, a first surface of an optically transmissive element, e.g., optical flat, lens, etc, is coated with a dielectric, anti-reflective coating (e.g., thin-film coatings or interference coatings). In one aspect, a single stack dielectric coat is applied. For example, coating techniques such as chemical vapor deposition (CVD), sputtering, physical vapor deposition, physical liquid deposition, chemical liquid deposition (e.g., electroplating) and others may be used as are well known. The optically transmissive element may be made of fused silica or other optically transmissive material. Coating step 110 may include coating the optical element with one or more layers of anti-reflective material. Useful anti-reflective coating materials, according to certain aspects, include oxide layers such as silicon dioxide ($SiO_2$), $TiO_2$, $Al_2O_3$ and tantalum oxide ($Ta_2O_5$), and/or other oxides including metal oxides, with appropriate thicknesses for the wavelength range of the radiation to be used. For dielectric coatings two materials with different index of refractions are needed. Another useful anti-reflective coating is a single coating of Magnesium Fluoride (MgF).

In step 115, a mask is provided to cover the portion of the first surface that will define the window portion. The mask may be a tape or other material as is well known, or it may include a tab or other element that is positioned to cover the window portion. One useful tape that works well in vacuum conditions is Kapton® Tape. In step 120, the first surface is coated with a dielectric, reflective coating (e.g., thin-film coatings or interference coatings) to create the mirror surface. For example, coating techniques such as CVD, sputtering, physical vapor deposition, physical liquid deposition, chemical liquid deposition (e.g., electroplating) and others may be used as are well known. This coating step may include coating the optical elements with one or more layers of reflective material. Useful reflective coating materials, according to certain aspects, include oxide layers such as silicon dioxide ($SiO_2$), $TiO_2$, $Al_2O_3$ and tantalum oxide ($Ta_2O_5$), and/or other oxides including metal oxides, with appropriate thicknesses. For dielectric reflective coatings two materials with different index of refractions are needed with appropriate thicknesses for the wavelength range of the radiation to be used. Other useful reflective coating materials, according to certain aspects, include metal coatings (i.e, gold, aluminum, silver, etc.). In step 125, the mask is removed to expose the window portion 20. For example, where the mask is a tab or other physical feature, the tab may simply be removed. Where the mask includes a chemical material or layer, the mask may be chemically removed using a solvent or other technique as is well known. It should be appreciated that, in step 110, only the first portion that will define the window portion of the first surface of the optical element need be processed (e.g., the remainder of the first surface may be masked).

Figure 3:
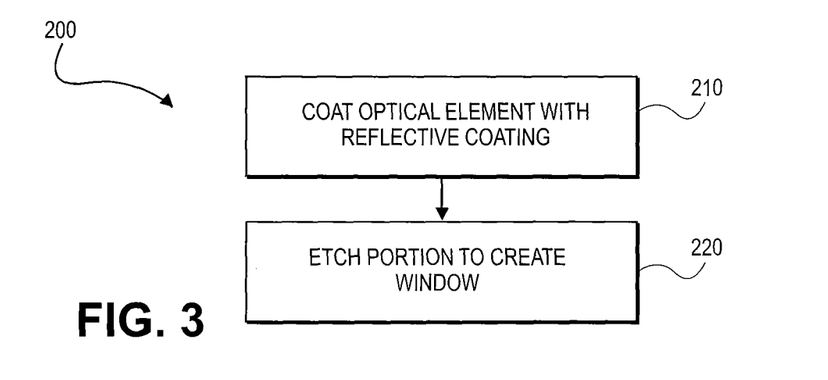
FIG. 3 illustrates a method of fabricating a mirror element having a window according to another embodiment.

FIG. 3 illustrates another method 200 of fabricating a mirror element 10 having a window 20 according to another embodiment. In step 210, the first surface is coated with a dielectric, reflective coating to create the mirror surface. For example, coating techniques such as CVD, electron beam deposition, sputtering and others as described above may be used as are well known. This coating step may include coating the optical elements with one or more layers of reflective material. Useful reflective coating materials, according to certain aspects, include oxide layers such as silicon dioxide ($SiO_2$), $TiO_2$, $Al_2O_3$ and tantalum oxide ($Ta_2O_5$), and/or metals or other oxides including metal oxides, with appropriate thicknesses. Thereafter, in step 220, a portion of the coated first surface is etched to remove the reflective coating and expose a window portion 20. Etching may include chemical etching, laser ablation or other techniques as are well known. In certain aspects, it is desirable that the window portion 20 have an anti-reflective coating. This advantageously helps prevent back reflections and reduce optical noise from passing through the first surface and in particular the defined window portion. Therefore, in certain aspects, an additional step of applying a dielectric, anti-reflective coating layer to the exposed window portion 20 is performed. For example, in one aspect, the reflective portion other than the window portion may be masked and an anti-reflective coating applied to the window portion after step 220. The mask is then removed as above. Alternatively, prior to step 210, an anti-reflective coating is applied to the optical element (or a portion thereof) similar to step 110 of FIG. 1. In this case, etching 220 is performed to expose the anti-reflective coating layer and define the shape of the window(s).

Figure 4:
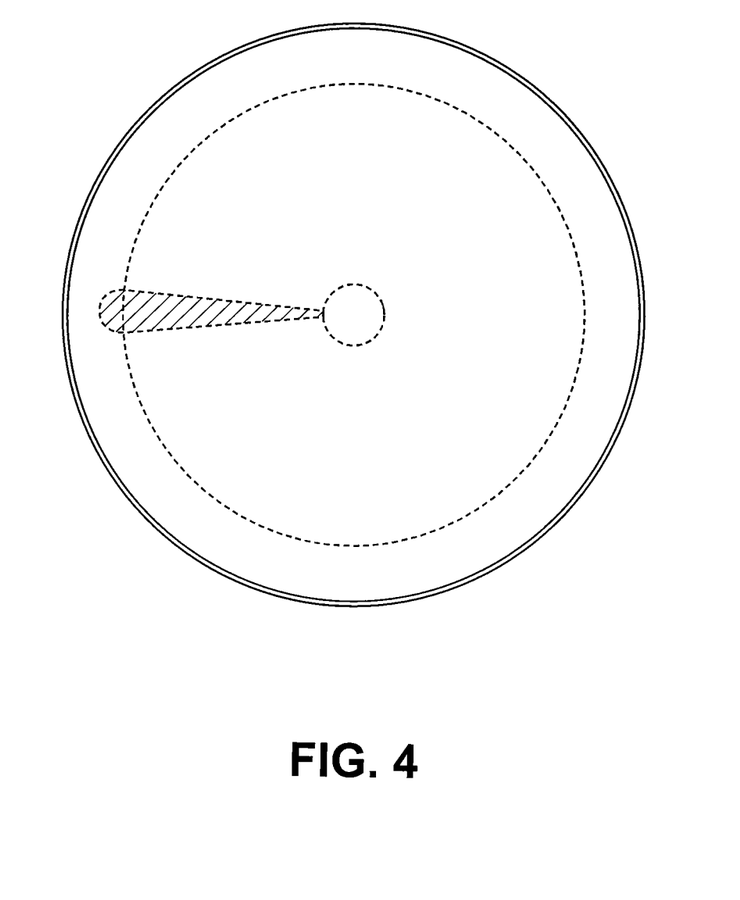
FIG. 4 illustrates an example of a mirror element having an elongated (wedge-shaped) window portion. The wedge shape is indicated by cross-hatching; the circular dotted lines represent optional curvature indicators (e.g., the element may be concave or convex between the indicators).
Figure 5:
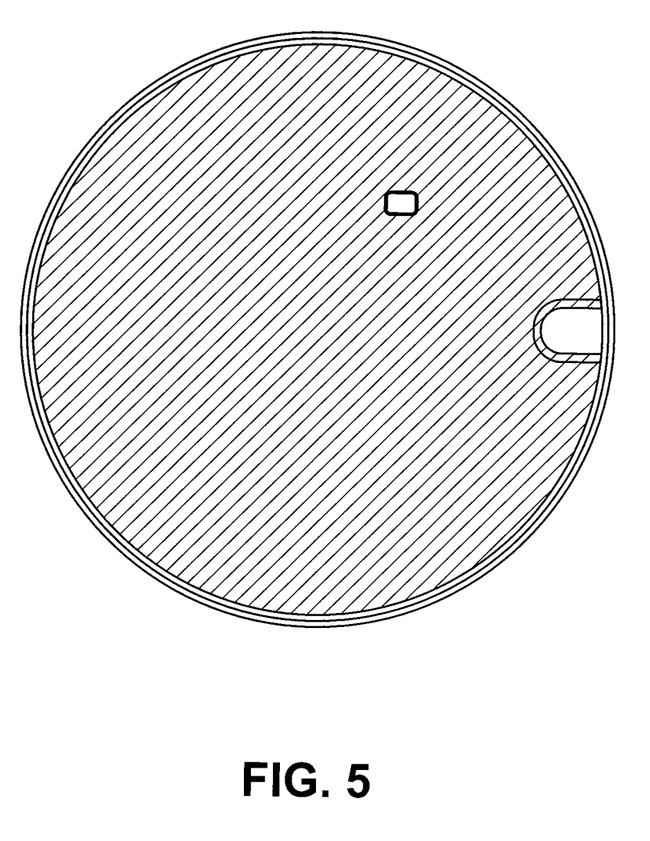
FIG. 5 illustrates an example of a mirror element having two separate window portions.

It should be appreciated that one or multiple windows may be formed on any given mirror surface, and the shape of window(s) 20 may be defined by the mask(s) and/or etch parameters used. For example, FIG. 4 illustrates an example of a mirror element having an elongated (wedge-shaped) window portion, and FIG. 5 illustrates an example of a mirror element having two separate window portions.

It should also be appreciated that the optical element may have any shape as desired. For example, for Herriott Cell applications it is desirable that the first surface (mirror surface) of the optical element have a concave shape (e.g., has a defined curvature profile). However, it is understood that the first surface may have or include a convex shaped surface, a flat shaped surface or other shaped surface. In one aspect, the first surface defines an interior surface of a sphere, such as may be found in an integrating sphere device, for example. Where the optical element has opposite surfaces (e.g., disk or lens element), the second surface of the optical element opposite the first surface may have any shape as desired, e.g., concave, flat, convex, etc. Additionally, the optical element may be in the shape of a prism, where the first surface (mirror surface) is substantially flat, or have any other shape as is desired. Further, more than one surface of an optical element may be processed according to the present invention to produce a mirrored surface (or portion of a surface) having one or more window elements defined therein.

The coatings applied can of course be tailored to the specific application(s) desired. For example, when applying a reflective coating, the reflectivity can be tailored as desired. As one example, a coating that provides for greater than about 99.9% reflectivity for wavelengths between 1645 to 1655 nm may be used. Similarly, for anti-reflective coatings, the reflectivity may be tailored as desired. As one example, an anti-reflective coating that provides for less than about 0.2% reflectivity for wavelengths between 1645 to 1655 nm may be used. One skilled in the art will recognize appropriate materials and process parameters for creating tailored reflective (and anti-reflective) coatings depending on the radiation wavelengths to be used.

Figure 6A:
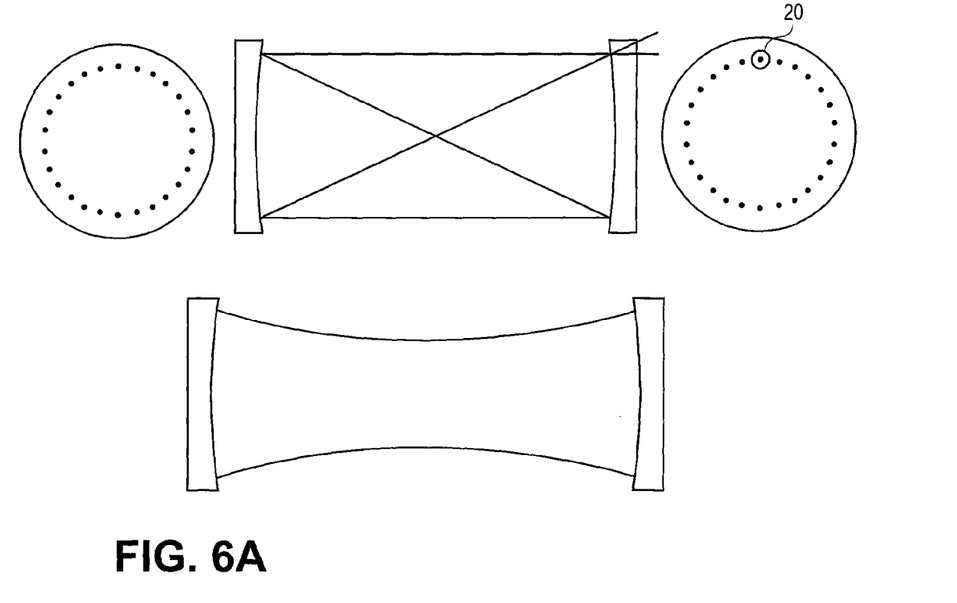
FIGS. 6A-C illustrate examples of different arrangements of optical elements defining a cavity.
Figure 6B:
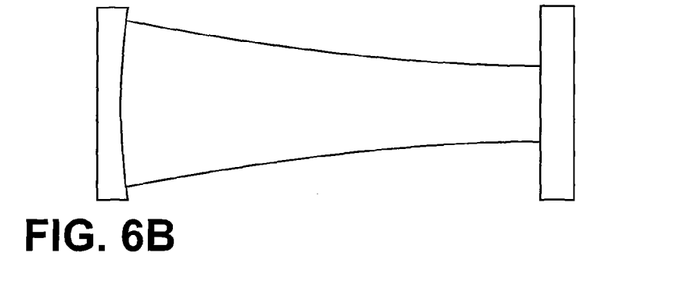
Figure 6C:
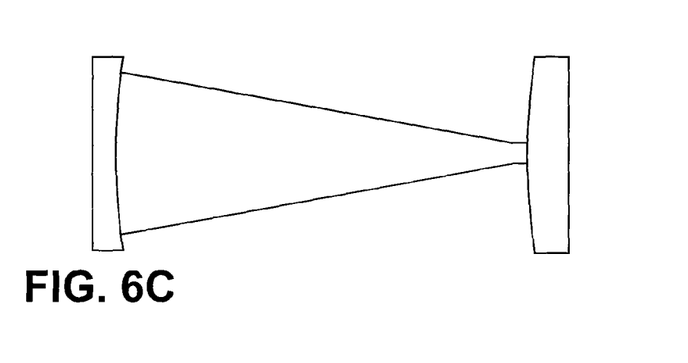

FIG. 6 illustrates examples of different arrangements of optical elements defining a cavity. As shown in FIG. 6a, a concave-concave arrangement is shown, where the beam enters the cavity through the defined window 20 and reflects off of discrete reflection points around each mirror element until the beam exits the entry point. FIG. 6b shows a concave-Plano arrangement and FIG. 6c shows a concave-convex arrangement.

Figure 7:
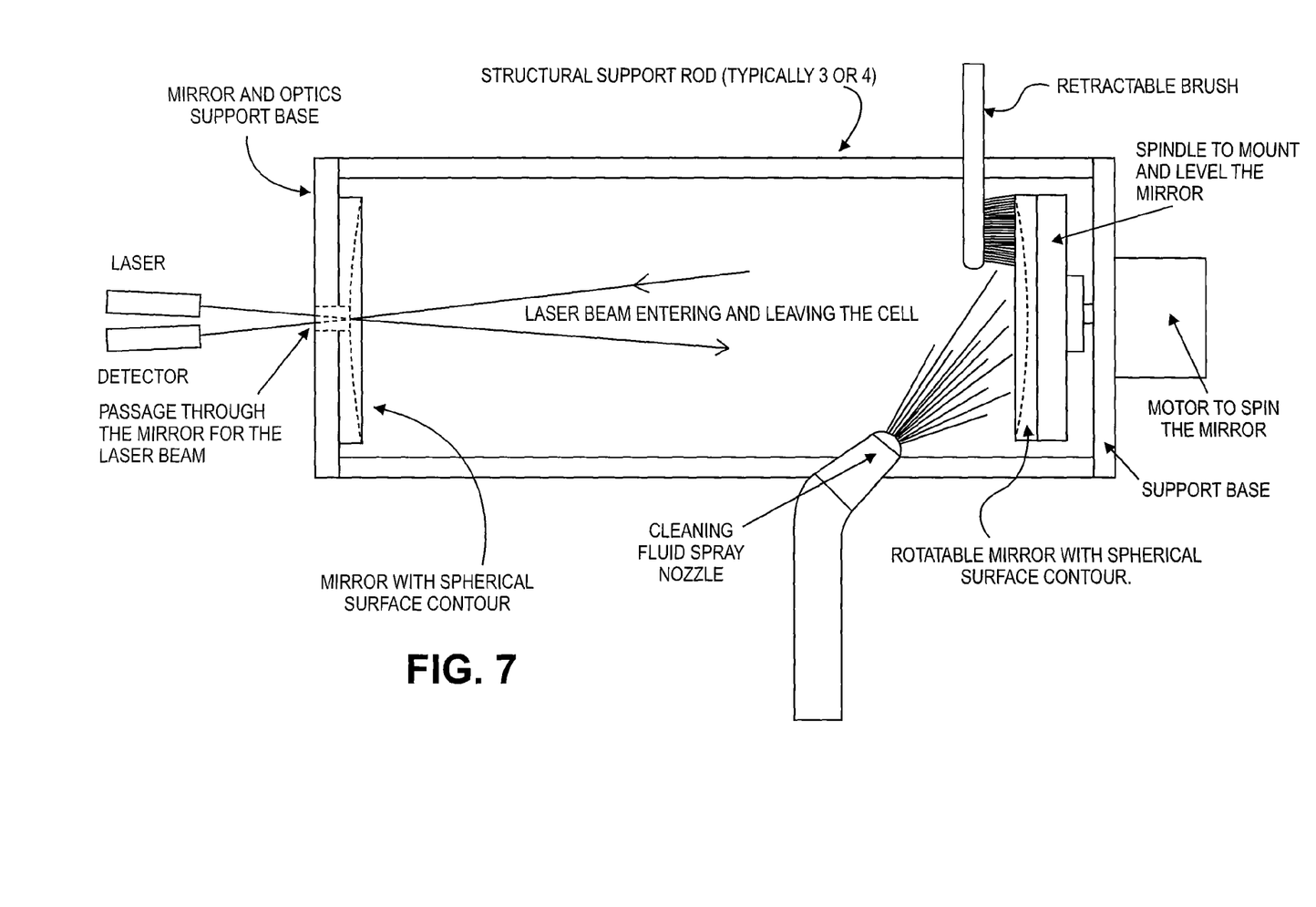
FIGS. 7 and 8 illustrate two Herriott Cell embodiments where mirror elements of the present invention are particularly useful.
Figure 8:
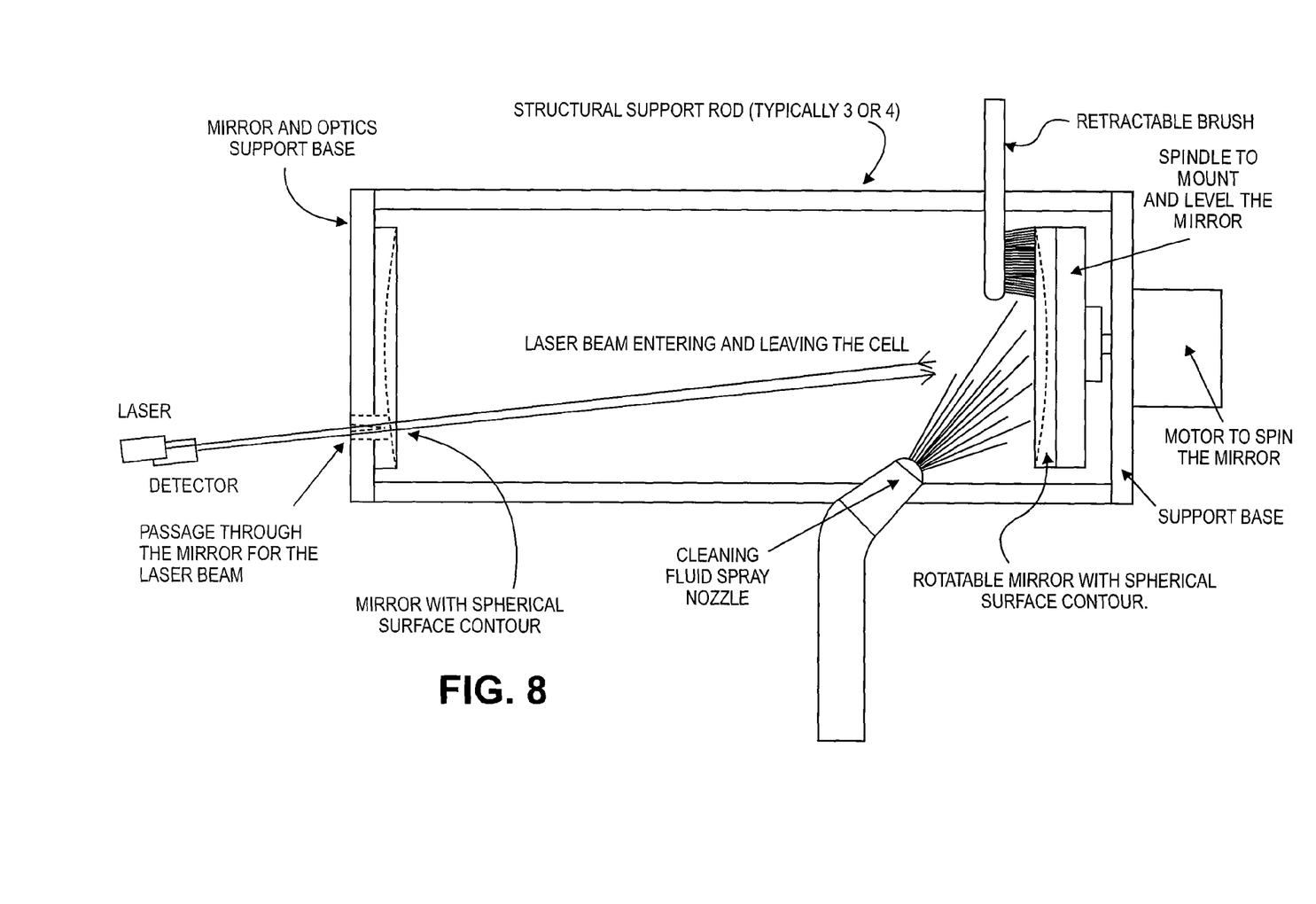

FIGS. 7 and 8 illustrate two Herriott Cell embodiments where mirror elements of the present invention are particularly useful. In the Herriott Cell arrangement of FIG. 7, the mirror element includes an entry aperture (e.g., window 20) defined in the center of the mirror element, along the axis of the device. The opposite mirror element rotates around the axis. An alternate fluid cleaning nozzle and brush are used to facilitate cleaning of the opposite mirror element. In FIG. 8, the entry aperture (e.g., window 20) is defined toward the periphery of the lens element as in FIG. 6a.

It should be appreciated that, as used herein, first surface does not necessarily mean the first surface that a ray of light encounters when interacting with an optical element; rather it refers to the surface that is being processed with reflective and/or anti-reflective coatings to form a mirror surface as discussed herein.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Embodiments can be used for a variety of optical devices including an integrating sphere, a Herriott cell, a White cell, a ring down cavity, an astigmatic Herriott cell, and other devices. Therefore, the scope of the appended claims should be accorded the broadest interpretation so as to encompass all such modifications and similar arrangements.

What is claimed is:

1. An optical cavity device, comprising:
 a first mirror element having an internal surface and an exterior surface, wherein a first portion of the internal surface comprises a reflective coating defining a reflective surface, and wherein a second portion of the internal surface comprises an anti-reflective coating defining an optically transmissive window portion of the internal surface, wherein the window portion is solid; and
 a second mirror element having an internal surface and an exterior surface; and
 a housing structure configured to hold the first and second mirror elements such that the internal surfaces of the first and second mirror elements are facing each other along a common axis and defining a cavity therebetween,
 wherein a radiation beam that enters the cavity through the optically transmissive window portion of the first mirror element and impinges on the internal surface of the second mirror element repeatedly reflects off of the internal surfaces of the first and second mirror elements multiple times before exiting the cavity through the optically transmissive window portion.

2. The optical cavity device of claim 1, wherein the internal surfaces of both the first and second mirror elements have a concave geometry.

3. The optical cavity element of claim 1, wherein the anti-reflective coating includes one or more layers of oxide material and/or a layer of MgF.

4. The optical cavity element of claim 1, wherein the reflective coating includes one or more layers of metal and/or oxide material.

5. The optical cavity device of claim 1, wherein the internal surface of the first mirror element is opposite the exterior surface of the first mirror element.

6. The optical cavity device of claim 1, wherein the first and second mirror elements are configured in a Herriott cell arrangement.

\* \* \* \* \*